(12) United States Patent
Berg et al.

(10) Patent No.: US 7,585,853 B2
(45) Date of Patent: Sep. 8, 2009

(54) COMPOUNDS HAVING SELECTIVE INHIBITING EFFECT AT GSK3

(75) Inventors: Stefan Berg, Sodertalje (SE); Sven Hellberg, Sodertalje (SE); Peter Soderman, Sodertalje (SE)

(73) Assignee: AstraZeneca AB, Sodertalje (SE)

( * ) Notice: Subject to any disclaimer, the term of this patent is extended or adjusted under 35 U.S.C. 154(b) by 480 days.

(21) Appl. No.: 10/539,543

(22) PCT Filed: Dec. 15, 2003

(86) PCT No.: PCT/SE03/01955

§ 371 (c)(1),
(2), (4) Date: Jun. 16, 2005

(87) PCT Pub. No.: WO2004/055005

PCT Pub. Date: Jul. 1, 2004

(65) Prior Publication Data

US 2006/0116362 A1    Jun. 1, 2006

(30) Foreign Application Priority Data

Dec. 17, 2002  (SE) .................................. 0203754

(51) Int. Cl.
| | | |
|---|---|---|
| A01N 43/00 | (2006.01) |
| A61K 31/00 | (2006.01) |
| A61K 31/4965 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 241/02 | (2006.01) |

(52) U.S. Cl. .............................. 514/210.2; 514/255.05; 514/255.06; 544/405; 544/406

(58) Field of Classification Search ........................ None
See application file for complete search history.

(56) References Cited

U.S. PATENT DOCUMENTS

| | | | |
|---|---|---|---|
| 6,255,307 B1 | 7/2001 | Cox et al. | |
| 2001/0031772 A1 | 10/2001 | Schoenafinger et al. | |
| 2004/0186113 A1* | 9/2004 | Berg et al. | 514/255.05 |
| 2006/0052396 A1* | 3/2006 | Berg et al. | 514/255.06 |
| 2006/0173014 A1* | 8/2006 | Berg et al. | 514/252.11 |

FOREIGN PATENT DOCUMENTS

| | | |
|---|---|---|
| WO | WO 0160806 A2 | 8/2001 |
| WO | WO 0168612 A2 | 9/2001 |
| WO | WO 02092585 A1 | 11/2002 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
International Search Report dated Apr. 20, 2004 for International Application No. PCT/SE2003/001955.
Caplus Accession No. 1997:637106, Document No. 127:293055, Saito, Tyota et al: "Solvent and substituent . . . analogs"; & Journal of Chem Society, Perkin Transactions 2:Physical Organic Chemistry (1997), 9, 1711-1716.
Caplus Accession No. 1968:50943, Document No. 68:50943, Rakusan, J. et al: "Aromatic diazo and azo compounds . . . ring"; & Collection of Czechosolvak Chemical Communications (1967), 32(8), 2882-9.

* cited by examiner

*Primary Examiner*—James O Wilson
*Assistant Examiner*—Jeffrey H Murray
(74) *Attorney, Agent, or Firm*—Kenneth F. Mitchell

(57) ABSTRACT

The present invention relates to new compounds of formula (I) wherein: Z is N and X is CH or N; Y is CONR$^5$; P is phenyl or a 5 or 6 membered heteroaromatic ring containing one or more heteroatoms selected from N, O or S; Q is phenyl or a 5 or 6 membered aromatic heterocyclic ring containing one or more nitrogen atoms; R is $C_{1-6}$alkylNR$^{10}$R$^{11}$ or $C_{1-6}$alkylazetidine; R$^{10}$ is hydrogen, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-61}$alkylheteroaryl or $C_{1-6}$alkylNR$^8$R$^9$; R$^{11}$ is $C_{1-6}$alkylNR$^8$R$^9$, $C_{0-6}$alkyl$C_{3-6}$cycloalkyl or $C_{0-6}$alkylheterocycloalkyl; as a free base or a pharmaceutically acceptable salt, solvate or solvate of salt thereof, a process for their preparation and new intermediates used therein, pharmaceutical formulations containing said therapeutically active compounds and to the use of said active compounds in therapy.

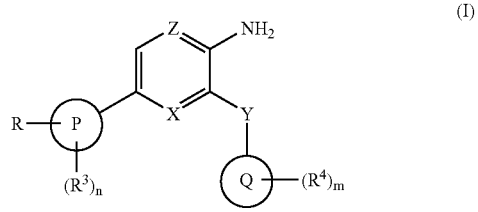

(I)

2 Claims, No Drawings

COMPOUNDS HAVING SELECTIVE INHIBITING EFFECT AT GSK3

FIELD OF THE INVENTION

The present invention relates to new compounds of formula I, as a free base or a pharmaceutically acceptable salt, solvate or solvate of salt thereof, to pharmaceutical formulations containing said compounds and to the use of said compounds in therapy. The present invention further relates to a process for the preparation of compounds of formula I and to new intermediates used therein.

BACKGROUND OF THE INVENTION

Glycogen synthase kinase 3 (GSK3) is a serine/threonine protein kinase composed of two isoforms (α and β), which are encoded by distinct genes but are highly homologous within the catalytic domain. GSK3 is highly expressed in the central and peripheral nervous system. GSK3 phosphorylates several substrates including tau, β-catenin, glycogen synthase, pyruvate dehydrogenase and elongation initiation factor 2b (eIF2b). Insulin and growth factors activate protein kinase B, which phosphorylates GSK3 on serine 9 residue and inactivates it.

Alzheimer's Disease (AD) Dementias, and Taupathies.

AD is characterized by cognitive decline, cholinergic dysfunction and neuronal death, neurofibrillary tangles and senile plaques consisting of amyloid-β deposits. The sequence of these events in AD is unclear, but is believed to be related. Glycogen synthase kinase 3β (GSK3β) or Tau (τ) phosphorylating kinase selectively phosphorylates the microtubule associated protein τ in neurons at sites that are hyperphosphorylated in AD brains. Hyperphosphorylated protein τ has lower affinity for microtubules and accumulates as paired helical filaments, which are the main components that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrophic lateral sclerosis, parkinsonism-dementia of Gaum, corticobasal degeneration, dementia pugilistica and head trauma, Down's syndrome, postencephalatic parkinsonism, progressive supranuclear palsy, Niemann-Pick's Disease and Pick's Disease. Addition of amyloid-β to primary hippocampal cultures results in hyperphosphorylation of τ and a paired helical filaments-like state via induction of GSK3β activity, followed by disruption of axonal transport and neuronal death (Imahori and Uchida., J. Biochem 121: 179-188, 1997). GSK3β preferentially labels neurofibrillary tangles and has been shown to be active in pre-tangle neurons in AD brains. GSK3 protein levels are also increased by 50% in brain tissue from AD patients. Furthermore, GSK3β phosphorylates pyruvate dehydrogenase, a key enzyme in the glycolytic pathway and prevents the conversion of pyruvate to acetyl-Co-A (Hoshi et al., PNAS 93:2719-2723, 1996). Acetyl-Co-A is critical for the synthesis of acetylcholine, a neurotransmitter with cognitive functions. Thus, GSK3β inhibition may have beneficial effects in progression as well as the cognitive deficits associated with Alzheimer's disease and other above-referred to diseases.

Chronic and Acute Neurodegenerative Diseases.

Growth factor mediated activation of the PI3K/Akt pathway has been shown to play a key role in neuronal survival. The activation of this pathway results in GSK3β inhibition. Recent studies (Bhat et. al., PNAS 97:11074-11079 (2000)) indicate that GSK3β activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3β. Thus GSK3β inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664-1668, 1996; Klein and Melton; PNAS 93:8455-8459, 1996). Inhibition of GSK3β may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry 2000 May; 157(5): 831-3) found that GSK3β levels were 41% lower in the schizophrenic patients than in comparison subjects. This study indicates that schizophrenia involves neurodevelopmental pathology and that abnormal GSK3 regulation could play a role in schizophrenia. Furthermore, reduced β-catenin levels have been reported in patients is exhibiting schizophrenia (Cotter et al., Neuroreport 9:1379-1383 (1998)).

Diabetes

Insulin stimulates glycogen synthesis in skeletal muscles via the dephosphorylation and thus activation of glycogen synthase. Under resting conditions, GSK3 phosphorylates and inactivates glycogen synthase via dephosphorylation. GSK3 is also over-expressed in muscles from Type II diabetic patients (Nikoulina et al., Diabetes 2000 February; 49(2): 263-71). Inhibition of GSK3 increases the activity of glycogen synthase thereby decreasing glucose levels by its conversion to glycogen. GSK3 inhibition may therefore be of therapeutic relevance in the treatment of Type I and Type II diabetes and diabetic neuropathy.

Hair Loss

GSK3 phosphorylates and degrades β-catenin. β-catenin is an effector of the pathway for keratonin synthesis. β-catenin stabilisation may be lead to increase hair development. Mice expressing a stabilised β-catenin by mutation of sites phosphorylated by GSK3 undergo a process resembling de novo hair morphogenesis (Gat et al., Cell 1998 Nov. 25; 95 (5):

605-14)). The new follicles formed sebaceous glands and dermal papilla, normally established only in embryogenesis. Thus GSK3 inhibition may offer treatment for baldness.

Oral Contraceptives

Vijajaraghavan et al. (Biol Reprod 2000 June; 62 (6):1647-54) reported that GSK3 is high in motile versus immotile sperm. Immunocytochemistry revealed that GSK3 is present in the flagellum and the anterior portion of the sperm head. These data suggest that GSK3 could be a key element underlying motility initiation in the epididymis and regulation of mature sperm function. Inhibitors of GSK3 could be useful as contraceptives for males.

DISCLOSURE OF THE INVENTION

The object of the present invention is to provide compounds having a selective inhibiting effect at GSK3 as well as having a good bioavailability. Accordingly, the present invention provides a compound of the formula I

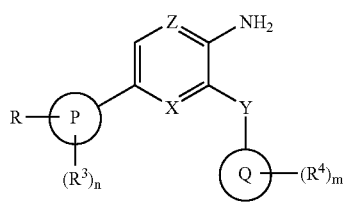

(I)

wherein:

Z is N;

Y is $CONR^5$, $NR^5CO$, $SO_2NR^5$, $NR^5SO_2$, $CH_2NR^5$, $NR^5CH_2$, $NR^5CONR^5$, $C_{1-6}$alkylene, $CH_2CO$, $COCH_2$, $CH=CH$, $OCH_2$ or $CH_2O$;

X is CH or N;

P is phenyl or a 5 or 6 membered heteroaromatic ring containing one or more heteroatoms independently selected from N, O or S and said phenyl ring or heteroaromatic ring may optionally be fused with a 5 or 6 membered saturated, partially saturated or unsaturated ring containing one or more atoms selected from C, N, O or S;

Q is phenyl or a 5 or 6 membered heteroaromatic ring containing one or more nitrogen atoms and said phenyl ring or heteroaromatic ring ring may optionally be fused with a 5 or 6 membered saturated, partially saturated or unsaturated ring containing one or more atoms selected from C, N, O or S;

R is $C_{1-6}$alkyl$NR^{10}R^{11}$ or $C_{1-6}$alkylazetidine which azetidine ring may be optionally substituted by A;

$R^3$ and $R^4$ are independently selected from halo, nitro, CHO, $C_{0-6}$alkylCN, $OC_{1-6}$alkylCN, $C_{0-6}$alkylOR$^6$, $OC_{1-6}$alkylOR$^6$, fluoromethyl, difluoromethyl, trifluoromethyl, fluoromethoxy, difluoromethoxy, trifluoromethoxy, $C_{0-6}$alkylNR$^6$R$^7$, $OC_{1-6}$alkylNR$^6$R$^7$, $OC_{1-6}$alkylOC$_{1-6}$alkylNR$^6$R$^7$, $NR^6$OR$^7$ $C_{0-6}$alkylCO$_2$R$^6$, $OC_{1-6}$alkylCO$_2$R$^6$, $C_{0-6}$alkylCONR$^6$R$^7$, $OC_{1-6}$alkylCONR$^6$R$^7$, $OC_{1-6}$alkylNR$^6$(CO)R$^7$, $C_{0-6}$alkylNR$^6$(CO)R$^7$, O(CO)NR$^6$R$^7$, NR$^6$(CO)OR$^7$, NR$^6$(CO)NR$^6$R$^7$, O(CO)OR$^6$, O(CO)R$^6$, $C_{0-6}$alkylCOR$^6$, $OC_{1-6}$alkylCOR$^6$, NR$^6$(CO)(CO)R$^6$, NR$^6$(CO)(CO)NR$^6$R$^7$, SR$^6$, $C_{0-6}$alkyl(SO$_2$)NR$^6$R$^7$, $OC_{1-6}$alkylNR$^6$(SO$_2$)R$^7$, $OC_{0-6}$alkyl(SO$_2$)NR$^6$R$^7$, $C_{0-6}$alkyl(SO)NR$^6$R$^7$, $OC_{1-6}$alkyl(SO)NR$^6$R$^7$, $SO_3R^6$, $C_{0-6}$alkylNR$^6$(SO$_2$)NR$^6$R$^7$, $C_{0-6}$alkylNR$^6$(SO)R$^7$, $OC_{1-6}$alkylNR$^6$(SO)R$^7$, $OC_{0-6}$alkylSO$_2$R$^6$, $C_{0-6}$alkylSO$_2$R$^6$, $C_{0-6}$alkylSOR$^6$, $C_{1-6}$alkyl, $C_{2-6}$alkenyl, $C_{2-6}$alkynyl, $C_{0-6}$alkylC$_{3-6}$cycloalkyl, $C_{0-6}$alkylaryl and $C_{0-6}$alkylheteroaryl, wherein any $C_{1-6}$alkyl, $C_{2-6}$alkenyl, $C_{2-6}$alkynyl, $C_{0-6}$alkylC$_{3-6}$cycloalkyl, $C_{0-6}$alkylaryl and $C_{0-6}$alkylheteroaryl may be optionally substituted by one or more A;

m is 0, 1, 2, 3 or 4;

n is 0, 1, 2, 3 or 4;

$R^5$ is hydrogen, $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl, $C_{1-6}$alkylNR$^6$R$^7$ or $C_{1-6}$alkylCONR$^6$R$^7$;

$R^6$ and $R^7$ are independently selected from hydrogen, $C_{1-6}$alkyl, (CO)OR$^8$, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl and $C_{1-6}$alkylNR$^8$R$^9$;

$R^6$ and $R^7$ may together form a substituted 5 or 6 membered heterocyclic ring containing one or more heteroatoms independently selected from N, O or S, which heterocyclic ring may be optionally substituted by A;

$R^8$ and $R^9$ are independently selected from hydrogen, $C_{1-6}$alkyl, $C_{2-6}$alkenyl, $C_{2-6}$alkynyl, $C_{0-6}$alkylC$_{3-6}$cycloalkyl, $C_{0-6}$alkylaryl and $C_{0-6}$alkylheteroaryl;

$R^8$ and $R^9$ may together form a 5 or 6 membered heterocyclic ring containing one or more heteroatoms independently selected from N, O or S, which heterocyclic ring may be optionally substituted by A;

$R^{10}$ is hydrogen, $C_{1-6}$alkyl, $C_{2-6}$alkenyl, $C_{2-6}$alkynyl, $C_{0-6}$alkylC$_{3-6}$cycloalkyl, $C_{0-6}$alkylaryl, $C_{0-6}$alkylheteroaryl or $C_{1-6}$alkylNR$^8$R$^9$;

$R^{11}$ is $C_{0-6}$alkylC$_{3-6}$cycloalkyl;

A is halo, nitro, CHO, CN, OR$^6$, $C_{1-6}$alkyl, $C_{2-6}$alkenyl, $C_{2-6}$alkynyl;

$C_{0-6}$alkylC$_{3-6}$cycloalkyl, fluoromethyl, difluoromethyl, trifluoromethyl, fluoromethoxy, difluoromethoxy, trifluoromethoxy, $C_{0-6}$alkylNR$^6$R$^7$, $OC_{1-6}$alkylNR$^6$R$^7$, $CO_2R^8$, CONR$^6$R$^7$, NR$^6$(CO)R$^6$, O(CO)R$^6$, COR$^6$, SR$^6$, (SO$_2$)NR$^6$R$^7$, (SO)NR$^6$R$^7$, SO$_3$R$^6$, SO$_2$R$^6$ or SOR$^6$;

as a free base or a pharmaceutically acceptable salt, solvate or solvate of salt thereof.

One aspect of the invention relates to compounds of formula I, wherein Z is N; Y is CONR$^5$; X is N; P is phenyl; Q is a 6 membered heteroaromatic ring containing one nitrogen atom; R is $C_{1-6}$alkylNR$^{10}$R$^{11}$; m is 0; n is 0; R$^5$ is hydrogen; R$^{10}$ is hydrogen or $C_{0-6}$alkylC$_{3-6}$cycloalkyl; $C_{0-6}$alkylaryl, $C_{0-6}$alkylheteroaryl or $C_{1-6}$alkylNR$^8$R$^9$; and R$^{11}$ is $C_{0-6}$alkylC$_{3-6}$cycloalkyl.

In one embodiment of this aspect there are provided compounds of formula I, wherein $C_{1-6}$alkyl in $C_{1-6}$alkylNR$^{10}$R$^{11}$ represents propyl; R$^{10}$ and R$^{11}$ represents cyclobutyl; and Q represents pyridin.

In another aspect of the invention the following compounds are provided:

3-Amino-6-{4-[3-(dicyclobutylamino)propyl]phenyl}-N-pyridin-3-ylpyrazine-2-carboxamide hydrochloride;

as a free base or an alternative pharmaceutically acceptable salt, solvate or solvate of salt thereof.

In yet another aspect of the invention the following compound, which is useful as intermediate in the preparation of compounds of formula I, is provided:

3-Amino-6-bromo-N-pyridin-3-ylpyrazine-2-carboxamide;

as a free base, a salt, solvate or solvate of a salt thereof.

In yet another aspect of the invention the following compound, which is useful as intermediate in the preparation of compounds of formula I, is provided:

N-[3-(4-Bromophenyl)propyl]-N,N-dicyclobutylamine;

as a free base, a salt, solvate or solvate of a salt thereof.

Listed below are definitions of various terms used in the specification and claims to describe the present invention.

For the avoidance of doubt it is to be understood that where in this specification a group is qualified by 'hereinbefore defined', 'defined hereinbefore', 'is as defined above' or 'are as defined above' the said group encompasses the first occurring and broadest definition as well as each and all of the preferred definitions for that group.

For the avoidance of doubt it is to be understood that in this specification '$C_{0-6}$' means a carbon group having 0, 1, 2, 3, 4, 5 or 6 carbon atoms.

In this specification, unless stated otherwise, the term "alkyl" includes both straight and branched chain alkyl groups. $C_{1-6}$alkyl may be methyl, ethyl, n-propyl, i-propyl, n-butyl, i-butyl, s-butyl, t-butyl, n-pentyl, i-pentyl, t-pentyl, neo-pentyl, hexyl.

The term "alkoxy" as used herein, unless stated otherwise includes "alkyl" O groups in which "alkyl" is as hereinbefore defined. $C_{1-5}$alkoxy may be methoxy, ethoxy, n-propoxy, i-propoxy, n-butoxy, i-butoxy, s-butoxy, t-butoxy, n-pentyloxy, i-pentyloxy, t-pentyloxy, neo-pentyloxy.

In this specification, unless stated otherwise, the term "alkenyl" includes both straight and branched chain alkenyl groups but references to individual alkenyl groups such as 2-butenyl is specific for the straight chain version only. Unless otherwise stated, the term "alkenyl" advantageously refers to chains with 2 to 5 carbon atoms, preferably 3 to 4 carbon atoms. Alkenyl may be, but are not limited to, vinyl, allyl, propenyl, i-propenyl, butenyl, i-butenyl, crotyl, pentenyl, i-pentenyl or hexenyl.

In this specification, unless stated otherwise, the term "alkynyl" includes both straight and branched chain alkynyl groups but references to individual alkynyl groups such as 2-butynyl are specific for the straight chain version only. Unless otherwise stated, the term "alkynyl" advantageously refers to chains with 2 to 5 carbon atoms, preferably 3 to 4 carbon atoms. Alkynyl may be, but are not limited to, ethynyl, propargyl, butynyl, i-butynyl, pentynyl, i-pentynyl or hexynyl.

In this specification, unless stated otherwise, the terms "aryl" refers to an optionally substituted monocyclic or bicyclic hydrocarbon ring system containing at least one aromatic ring. The "aryl" may be fused with a $C_{5-7}$cycloalkyl ring to form a bicyclic hydrocarbon ring system. Examples and suitable values of the term "aryl" are phenyl, naphthyl, indanyl or tetralinyl.

In this specification, unless stated otherwise, the terms "heteroaryl" and "5 or 6 membered heteroaromatic ring" containing one or more heteroatoms selected from N, O and S may be, but are not limited to, furyl, imidazolyl, isoxazolyl, isothiazolyl, oxazolyl, pyrazinyl, pyrazolyl, pyridazinyl, pyridyl, pyrimidyl, pyrrolyl, thiazolyl or thienyl In this specification, unless stated otherwise, the term "5 or 6 membered saturated, partly saturated or unsaturated ring containing atoms independently selected from C, N, O or S" may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, cyclohexyl or cyclopentyl.

In this specification, unless stated otherwise, the term "5 or 6 membered heteroaromatic ring containing one or more heteroatoms independently selected from N, O, or S" may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl or imidazolyl.

In this specification, unless stated otherwise, the term halogen may be fluorine, chlorine, bromine or iodine.

The present invention relates to the use of compounds of formula I as hereinbefore defined as well as to the salts thereof. Salts for use in pharmaceutical compositions will be pharmaceutically acceptable salts, but other salts may be useful in the production of the compounds of formula I.

Both organic and inorganic acids can be employed to form non-toxic pharmaceutically acceptable acid addition salts of the compounds of this invention. In addition, a suitable pharmaceutically acceptable salt of the compounds of the invention, which is sufficiently acidic is an alkali metal salt, an alkaline earth metal salt or a salt with an organic base, which affords a physiologically-acceptable cation.

Some compounds of formula I may have chiral centres and/or geometric isomeric centres (E- and Z-isomers), and it is to be understood that the invention encompasses all such diastereoisomers, optical and geometric isomers that possess GSK3 inhibitory activity.

It is to be understood that the present invention relates to any and all tautomeric forms of the compounds of formula I.

An object of the invention is to provide compounds of formula I for therapeutic use, especially compounds that are useful for the prevention and/or treatment of conditions associated with glycogen synthase kinase-3 (GSK3) in mammals including man. Particularly, compounds of formula I exhibiting a selective affinity for GSK-3.

Methods of Preparation

Another aspect of the present invention provides a process for preparing a compound of formula I as a free base or a pharmaceutically acceptable salt thereof.

Throughout the following description of such processes it is understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis" T. W. Green, P. G. M. Wuts, Wiley-Interscience, New York, 1999.

Methods of Preparation of Intermediates

The process for the preparation of the intermediates, wherein Y, X, Z, P, Q, R, $R^1$, $R^2$, $R^3$, $R^4$, $R^5$, $R^6$, $R^7$, $R^8$, $R^9$, $R^{10}$, $R^{11}$, $R^{12}$, A, m and n are, unless specified otherwise, defined as in formula I, comprises of:

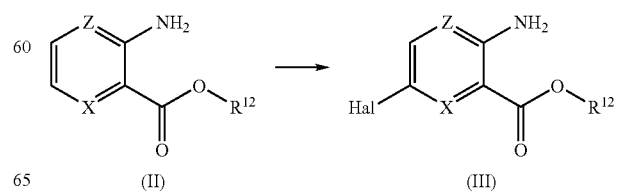

(i) halogenation of a compound of formula II, wherein Z is N and X are N or CH, $R^{12}$ is hydrogen, $C_{1-6}$alkyl or when $R^{12}$ is hydrogen in the form of a salt such as a sodium salt, to obtain a compound of formula III, may be carried out using a suitable halogenating reagent such as iodine, bromine, chlorine, halide salts such as ICl, BrCl or HOCl or other suitable halogenation reagents such as N-bromosuccinimide or phosphorous tribromide. The reaction may be catalysed by metals or acids such as Fe, Cu-salts, acetic acid or sulfuric acid or aided by oxidising agents such as nitric acid, hydrogen peroxide or sulfur trioxide. The reaction may be carried out in a suitable solvent such as water, acetic acid or chloroform at a temperature in the range of –70° C. to +100° C.

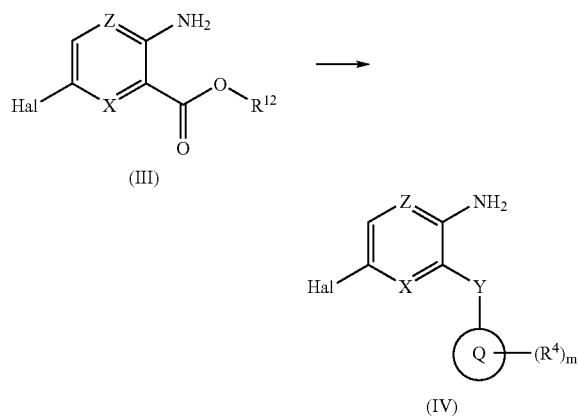

(ii) amidation of a compound of formula III, wherein Z is N and X are N or CH, $R^{12}$ is $C_{1-6}$alkyl to obtain a compound of formula IV, wherein Y is $CONR^5$ may be carried out by treating a compound of formula III with the appropriate amine such as a compound of formula V,

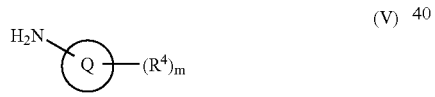

wherein Q, $R^4$ and m is as defined above. The reaction may be performed neat or using a suitable solvent such as N,N-dimethylformamide, methylene chloride or ethyl acetate at a temperature ranging from –25° C. to +150° C. The reaction may be aided by using a base such as potassium carbonate, trietylamine or 1,8-diazabicyclo[5.4.0]undec-7-ene or an acid such as trimethylaluminum or p-toulenesulfonic acid.

(iii) amidation of a compound of formula III, wherein $R^{12}$ is hydrogen, to obtain a compound of formula IV, wherein Y is $CONR^5$ and $R^4$ is a substituent that is not susceptible to certain coupling agents, may be performed by activation of a compound of formula III by treating the compound with coupling reagents such as 1,3-diisopropylcarbodiimide, 1-[3-(dimethylamino)propyl]-3-ethylcarbodiimide hydrochloride, 1,3-dicyclohexylcarbodiimide, O-(benzotriazol-1-yl)-N,N,N',N'-tetramethyluronium tetrafluoroborate, O-(benzotriazol-1-yl)-N,N,N',N'-tetramethyluronium hexafluorophosphate, 1,1'-carbonyldiimidazole or O-(7-azabenzotriazol-1-yl)-N,N,N',N'-tetramethyluronium hexafluorophosphate where the reaction may be aided by the addition of 1-hydroxybenzotriazole hydrate, or using an acyl halide reagent such as cyanuric chloride, oxalyl chloride, thionyl chloride or bromotripyrrolidinophosphonium hexafluorophosphate, followed by treatment with the appropriate amine such as a compound of formula V, in a suitable solvent such as methylene chloride chloroform, acetonitrile or tetrahydrofuran and at a reaction temperature between 0° C. and reflux. The reaction may be aided by using a base such as potassium carbonate or a trialkyl amine e.g triethyl amine or N-ethyl-N, N-diisopropyl amine

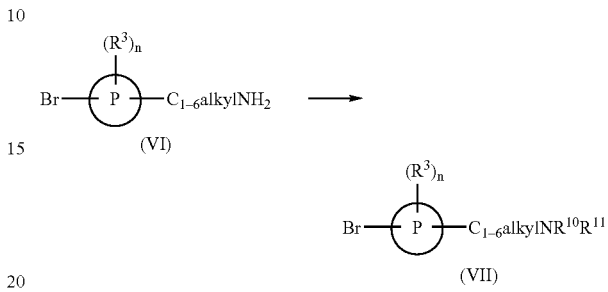

(iv) conversion of a compounds of formula VI, wherein P, $R^3$, n and $C_{1-6}$alkyl are as defined above, to a compound of formula VII, wherein P, $R^3$, $R^{10}$, $R^{11}$, n and $C_{1-6}$alkyl are as defined above, may be carried out by the reaction with a appropriate aldehyde ($R^{10}CHO$ and/or $R^{11}CHO$) and/or a ketone ($R^{10}(CO)R^{11}$) in a suitable solvent such as methylene chloride, chloroform, dichloroethane or methanol in the precense of a suitable acid such as acetic acid followed by the addition of a suitable reducing agent such as sodium cyanoborohydride or sodium triacetoxy borohydride and at a reaction temperature between 0° C. and +50° C.

Methods of Preparation of End Products

Another object of the invention are processes for the preparation of a compound of general formula I, wherein Y, X, Z, P, Q, R, $R^1$, $R^2$, $R^3$, $R^4$, $R^5$, $R^6$, $R^7$, $R^8$, $R^9$, $R^{10}$, $R^{11}$, A, m and n are, unless specified otherwise, defined as in formula I, comprising of:

A de-halogen coupling, wherein $R^3$ and $R^4$ are substituents that are not susceptible to certain agents in the reaction, of a compound of formula IV with a appropriate aryl species to give a compound of formula I:

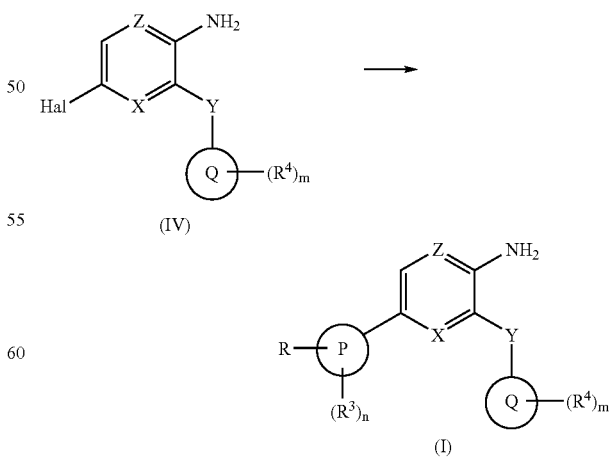

Thus, the de-halogen coupling according to process A may be carried out by coupling of a compound of formula IV with an appropriate aryl boronic acid or a boronic ester. The reaction may be carried out using a suitable palladium catalyst such as Pd(PPh$_3$)$_4$, Pd(dppf)Cl$_2$ or Pd(OAc)$_2$ with or without a ligand such as P(tert-butyl)$_3$ or, 2-(dicyclohexylphosphino) biphenyl or a nickel catalyst such as nickel on charcoal or Ni(dppe)Cl$_2$ together with Zn and sodium triphenylphosphinetrimetasulfonate. A suitable base such as an alkyl amine e.g. triethylamine, or potassium carbonate, sodium carbonate, sodium hydroxide or cesium fluoride may be used in the reaction, which is performed in the temperature range between +20° C. and +160° C. using an oil bath or in a microwave oven in a suitable solvent or solvent mixture such as toluene, tetrahydrofuran, dimethoxyethane/water or N,N-dimethylformamide. The aryl boronic acid or a boronic ester may be formed from a compound of formula VII using a suitable base such as butyl lithium and a suitable boron compound such as trimethyl borate or triisopropyl borate. The reaction may be performed in an aprotic solvent e.g. tetrahydrofuran or hexane in a temperature range between −78° C. and +20° C.;

The hydrochloric salt of compound of formula I may be obtained from a compound of formula I by treatment with hydrochloric acid at a temperature range between 0° C. and +25° C., in suitable solvent such as methylene chloride, tetrahydrofuran or methylene chloride/methanol mixture.

WORKING EXAMPLES

Example 1

3-Amino-6-bromo-N-pyridin-3-ylpyrazine-2-carboxamide

To 3-aminopyridine (10 g, 106 mmol) at 70° C. were added methyl 3-amino-6-bromo-2-pyrazinecarboxylate (1.0 g, 4.3 mmol) and 1,8-diazabicyclo[5.4.0]undec-7-ene (645 μL, 4.3 mmol). The reaction solution was stirred for 4 h, diluted with water (75 mL) and extracted with methylene chloride. The combined organic layers were washed with a saturated ammonium chloride solution, dried (MgSO$_4$), filtered and evaporated in vacuo. The crude product was purified on a silica gel column using methylene chloride/ethanol, (9:1), as the eluent to give 750 mg (59% yield) of the title compound as a yellow solid: $^1$H NMR (CDCl$_3$, 400 MHz) δ 9.50 (br s, 1H), 8.82 (d, J=3 Hz, 1H), 8.43 (dd, J=5 and 1 Hz, 1H), 8.31 (s, 1H), 8.23 (ddd, J=8, 3 and 2 Hz, 1H), 7.34 (dd, J=8, 5 Hz, 1H); MS (TSP) m/z 294 (M$^+$+1).

Example 2

N-[3-(4-Bromophenyl)propyl]-N,N-dicyclobutylamine 3-(4-Bromophenyl)propan-1-amine (0.50 g, 2.34 mmol; described in: Davies, R. V. et al. *J. Chem. Soc. Perkin Trans.* 1 1977, 2357-2364), cyclobutanone (0.393 g, 5.61 mmol) and acetic acid (0.140 mL, 2.34 mmol) were mixed in dichloroethane (6 mL) and stirred for 30 min. Sodium triacetoxy borohydride was added and the reaction mixture was stirred for 15 h. The reaction was quenched with water (15 mL) and extracted with methylene chloride (50 mL). The organic phase was separated, dried and evaporated. Purification by column chromatography using methylene chloride to methylene chloride/methanol, (2:1), gradient as the eluent gave 0.32 g (42% yield) of the title compound as colorless oil: MS (ESI) m/z 322 and 324 (M$^+$+1).

Example 3

3-Amino-6-{4-[3-(dicyclobutylamino)propyl]phenyl}-N-pyridin-3-ylpyrazine-2-carboxamide Hydrochloride n-Butyllithium (0.97 mL, 1.55 mmol) was added dropwise over 20 min to a cooled (−78° C.) solution of N-[3-(4-bromophenyl)propyl]-N,N-dicyclobutylamine (0.10 g, 0.31 mmol) and triisopropyl borate (0.21 mL, 0.93 mmol) in anhydrous tetrahydrofuran (2 mL) under a nitrogen atmosphere. The reaction mixture was stirred for 2 h at −78° C. HCl (aq 3 M, 0.6 mL) was added to the reaction mixture and the mixture was allowed to warm to room temperature. Tetrahydrofuran (2 mL) was added, followed by sodium carbonate (1.1 g, 10.8 mmol), Pd(dppf)Cl$_2$ (0.010 g, 12.2 μmol) and 3-amino-6-bromo-N-pyridin-3-ylpyrazine-2-carboxamide (0.10 g, 0.34 mmol). The mixture was heated to 65° C. for 15 h. The solvent was removed and purification by column chromatography on silica using a gradient methylene chloride to methylene chloride/methanol, (2:1), as the eluent gave a yellow solid. The solid was dissolved in methylene chloride (10 mL) and 1 M HCl in diethyl ether was added while stirring. The formed yellow precipitate was filtered and dried to give 75 mg (53% yield) of the title compound as yellow solid: $^1$H NMR (D$_2$O, 400 MHz) δ 9.47 (s, 1H), 8.73 (s, 1H), 8.69 (d, J=8.6 Hz, 1H), 8.61 (d, J=5.6 Hz, 1H), 8.10 (dd, J=15, 6 Hz, 1H), 7.98 (d, J=9 Hz, 2H), 7.41 (d, J=9 Hz, 2H), 3.80 (m, 2H), 3.01 (m, 2H), 2.75 (m, 2H), 2.28 (m, 4H), 2.17 (m, 4H), 2.03 (m, 2H), 1.79 (m, 4H); MS (ESI) 457 m/z (M$^+$+1).

Pharmaceutical Compositions

According to one aspect of the present invention there is provided a pharmaceutical composition comprising a compound of formula I, as a free base or a pharmaceutically acceptable salt, solvate or solvate of salt thereof, for use in the prevention and/or treatment of conditions associated with glycogen synthase kinase-3.

The composition may be in a form suitable for oral administration, for example as a tablet, for parenteral injection as a sterile solution or suspension. In general the above compositions may be prepared in a conventional manner using pharmaceutically carriers or diluents. Suitable daily doses of the compounds of formula I in the treatment of a mammal, including man, are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

A compound of formula I, or a pharmaceutically acceptable salt, solvate or solvate of salt thereof, can be used on its own but will usually be administered in the form of a pharmaceutical composition in which the formula I compound/salt/solvate (active ingredient) is in association with a pharmaceutically acceptable diluent or carrier. Dependent on the mode of administration, the pharmaceutical composition may comprise from 0.05 to 99% w (percent by weight), for example from 0.10 to 50% w, of active ingredient, all percentages by weight being based on total composition.

A diluent or carrier includes water, aqueous polyethylene glycol, magnesium carbonate, magnesium stearate, talc, a sugar (such as lactose), pectin, dextrin, starch, tragacanth, microcrystalline cellulose, methyl cellulose, sodium carboxymethyl cellulose or cocoa butter.

A composition of the invention can be in tablet or injectable form. The tablet may additionally comprise a disintegrant and/or may be coated (for example with an enteric coating or coated with a coating agent such as hydroxypropyl methylcellulose).

The invention further provides a process for the preparation of a pharmaceutical composition of the invention which comprises mixing a compound of formula I, or a pharmaceutically acceptable salt, solvate or solvate of salt thereof, a hereinbefore defined, with a pharmaceutically acceptable diluent or carrier.

An example of a pharmaceutical composition of the invention is an injectable solution containing a compound of the invention, or a a pharmaceutically acceptable salt, solvate or solvate of salt thereof, as hereinbefore defined, and sterile water, and, if necessary, either sodium hydroxide or hydrochloric acid to bring the pH of the final composition to about pH 5, and optionally a surfactant to aid dissolution.

Liquid solution comprising a compound of formula I, or a salt thereof, dissolved in water.

| Solution | mg/mL |
|---|---|
| Compound X | 5.0% w/v |
| Pure water | To 100% |

Medical Use

Surprisingly, it has been found that the compounds defined in the present invention, as a free base or a pharmaceutically acceptable salt thereof, are well suited for inhibiting glycogen synthase kinase-3 (GSK3). Accordingly, the compounds of the present invention are expected to be useful in the prevention and/or treatment of conditions associated with glycogen synthase kinase-3 activity, i.e. the compounds may be used to produce an inhibitory effect of GSK3 in mammals, including man, in need of such prevention and/or treatment.

GSK3 is highly expressed in the central and peripheral nervous system and in other tissues. Thus, it is expected that compounds of the invention are well suited for the prevention and/or treatment of conditions associated with glycogen synthase kinase-3 in the central and peripheral nervous system. In particular, the compounds of the invention are expected to be suitable for prevention and/or treatment of conditions associated with especially, dementia, Alzheimer's Disease, Parkinson's Disease, Frontotemporal dementia Parkinson's Type, Parkinson dementia complex of Guam, HIV dementia, diseases with associated neurofibrillar tangle pathologies and dementia pugilistica.

Other conditions are selected from the group consisting of amyotrophic lateral sclerosis, corticobasal degeneration, Down syndrome, Huntington's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, schizophrenia, cognitive disorders, hair loss and contraceptive medication.

Further conditions are selected from the group consisting of predemented states, Mild Cognitive Impairment, Age-Associated Memory Impairment, Age-Related Cognitive Decline, Cognitive Impairment No Dementia, mild cognitive decline, mild neurocognitive decline, Late-Life Forgetfulness, memory impairment and cognitive impairment, vascular dementia, dementia with Lewy bodies, Frontotemporal dementia and androgenetic alopecia and Type I and Type II diabetes, diabetic neuropathy and diabetes related disorders.

One embodiment of the invention relates to the prevention and/or treatment of dementia and Alzheimer's Disease.

The dose required for the therapeutic or preventive treatment of a particular disease will necessarily be varied depending on the host treated, the route of administration and the severity of the illness being treated.

The present invention relates also to the use of a compound of formula I as defined hereinbefore, in the manufacture of a medicament for the prevention and/or treatment of conditions associated with glycogen synthase kinase-3.

In the context of the present specification, the term "therapy" also includes "prevention" unless there are specific indications to the contrary. The terms "therapeutic" and "therapeutically" should be construed accordingly.

The invention also provides for a method of treatment and/or prevention of conditions associated with glycogen synthase kinase-3 comprising administering to a mammal, including man in need of such treatment and/or prevention a therapeutically effective amount of a compound of formula I, as hereinbefore defined.

Non-Medical Use

In addition to their use in therapeutic medicine, the compounds of formula I as a free base or a pharmaceutically acceptable salt thereof, are also useful as pharmacological tools in the development and standardisation of in vitro and in vivo test systems for the evaluation of the effects of inhibitors of GSK3 related activity in laboratory animals such as cats, dogs, rabbits, monkeys, rats and mice, as part of the search for new therapeutics agents.

Pharmacology

Determination of ATP Competition in Scintillation Proximity GSK3β Assay.

GSK3β Scintillation Proximity Assay.

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser($PO_3H_2$)-Pro-Gln-Leu (AstraZeneca, Lund), was added at a final concentration of 1 µM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptoethanol, 0.004% Brij 35 (a natural detergent), 0.5% glycerol and 0.5 µg BSA/25 µl. The reaction was initiated by the addition of 0.04 µCi [γ-$^{33}$P]ATP (Amersham, UK) and unlabelled ATP at a final concentration of 1 µM and assay volume of 25 µl. After incubation for 20 minutes at room temperature, each reaction was terminated by the addition of 25 µl stop solution containing 5 mM EDTA, 50 µM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK3β, used to calculate the inhibition constants ($K_i$) of the various compounds, was 20 µM.

The following abbreviations have been used:

| MOPS | Morpholinepropanesulfonic acid |
|---|---|
| EDTA | Ethylenediaminetetraacetic acid |

| | |
|---|---|
| BSA | Bovin Serum Albumin |
| ATP | Adenosine Triphosphate |
| SPA | Scintillation Proximity Assay |
| GSK3 | Glycogen synthase kinase 3 |

Results

Typical $K_i$ values for the compounds of the present invention are in the range of about 0.001 to about 10,000 nM. Other values for $K_i$ are in the range of about 0.001 to about 1000 nM. Further values for $K_i$ are in the range of about 0.001 nM to about 300 nM.

The invention claimed is:

1. A compound selected from the group consisting of:
    3-Amino-6-{4-[3-(dicyclobutylamino)propyl]phenyl}-N-pyridin-3-ylpyrazine-2-carboxamide hydrochloride;
    a free base thereof, and a pharmaceutically acceptable salt of said free base.

2. A pharmaceutical formulation comprising as active ingredient a therapeutically effective amount of a compound according to claim 1 in association with pharmaceutically acceptable carriers or diluents.

* * * * *

UNITED STATES PATENT AND TRADEMARK OFFICE
CERTIFICATE OF CORRECTION

PATENT NO. : 7,585,853 B2　　　　　　　　　　　　　　　　　　　　　　　Page 1 of 1
APPLICATION NO. : 10/539543
DATED : September 8, 2009
INVENTOR(S) : Berg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 928 days.

Signed and Sealed this

Fourteenth Day of September, 2010

David J. Kappos
*Director of the United States Patent and Trademark Office*